United States Patent
Majeed

(10) Patent No.: US 8,119,696 B2
(45) Date of Patent: Feb. 21, 2012

(54) TREATMENT OF SUPERFICIAL AND CUTANEOUS MYCOSES WITH A PURE FORM OF 1,7-BIS(4-HYDROXY-3-METHOXYPHENYL)-3,5-HEPTANEDIONE

(75) Inventor: Muhammed Majeed, Piscataway, NJ (US)

(73) Assignee: Muhammed Majeed, Edison, NJ (US)

( * ) Notice: Subject to any disclaimer, the term of this patent is extended or adjusted under 35 U.S.C. 154(b) by 293 days.

(21) Appl. No.: 12/142,879

(22) Filed: Jun. 20, 2008

(65) Prior Publication Data
US 2009/0275665 A1    Nov. 5, 2009

Related U.S. Application Data

(60) Provisional application No. 60/945,254, filed on Jun. 20, 2007.

(51) Int. Cl.
*A61K 31/12*    (2006.01)
*A61K 31/05*    (2006.01)
*A01N 35/00*    (2006.01)
*A01N 31/08*    (2006.01)

(52) U.S. Cl. ........................ 514/679; 514/734

(58) Field of Classification Search ......... None
See application file for complete search history.

(56) References Cited

OTHER PUBLICATIONS

Pan et al., Drug Metab and Disposition 27:486-494, 1999.*
Tsao et al. (Journal of Food and Drug Analysis, 8(3): 208-212, 2000).*
Apisariyakul et al. (Journal of Ethnopharmacology, 49:163-169, 1995).*

* cited by examiner

*Primary Examiner* — James D Anderson
*Assistant Examiner* — Bong-Sook Baek

(57) ABSTRACT

Disclosed are novel and enhanced anti-fungal properties of greater than 99% pure form of 1,7-Bis(4-hydroxy-3-methoxyphenyl)-3,5-heptanedione in comparison with the corresponding 95% pure form, said greater than 99% pure form of 1,7-Bis(4-hydroxy-3-methoxyphenyl)-3,5-heptanedione being devoid of 5-Hydroxy-1,7-bis(4-hydroxy-3-methoxyphenyl)-3-heptanone and 3,5-Dihydroxy-1,7-bis(4-hydroxy-3-methoxyphenyl)-heptane. The inventors disclose the uses of greater than 99% pure form of 1,7-Bis(4-hydroxy-3-methoxyphenyl)-3,5-heptanedione as anti-fungal agents capable of inhibiting superficial and cutaneous mycoses in humans and treatment methods thereof. Also disclosed is the enhanced potential of greater than 99% pure form of 1,7-Bis(4-hydroxy-3-methoxyphenyl)-3,5-heptanedione as compared to the corresponding 95% pure form against bacterial and fungal phytopathogens and applications thereof in agriculture.

4 Claims, 3 Drawing Sheets

Fig. 1 Observation of Anti Dermatophytic Activity of Compound TP

Fig. 2 Observation of Anti Dermatophytic Activity of Compound SW

TREATMENT OF SUPERFICIAL AND CUTANEOUS MYCOSES WITH A PURE FORM OF 1,7-BIS(4-HYDROXY-3-METHOXYPHENYL)-3,5-HEPTANEDIONE

BACKGROUND OF THE INVENTION

This application is a non-provisional filing of provisional application No. 60/945,254, filed on Jun. 20, 2007 the contents of which are incorporated herein by reference.

FIELD OF THE INVENTION

The present invention in general relates to 1,7-Bis (4-hydroxy-3-methoxyphenyl)-3,5-heptanedione and its applications. More specifically, the present invention relates to novel and enhanced anti-fungal properties of greater than 99% pure form of 1,7-Bis(4-hydroxy-3-methoxyphenyl)-3,5-heptanedione in comparison with the corresponding 95% pure form, said greater than 99% pure form of 1,7-Bis(4-hydroxy-3-methoxyphenyl)-3,5-heptanedione being devoid of 5-Hydroxy-1,7-bis(4-hydroxy-3-methoxyphenyl)-3-heptanone and 3,5-Dihydroxy-1,7-bis(4-hydroxy-3-methoxyphenyl)-heptane. The inventors disclose the uses of greater than 99% pure form of 1,7-Bis(4-hydroxy-3-methoxyphenyl)-3,5-heptanedione as anti-fungal agents capable of inhibiting superficial and cutaneous mycoses in humans and treatment methods thereof. Also disclosed is the enhanced potential of greater than 99% pure form of 1,7-Bis(4-hydroxy-3-methoxyphenyl)-3,5-heptanedione as compared to the corresponding 95% pure form against bacterial and fungal phytopathogens and applications thereof in agriculture. Fungal infections are responsible for several disease conditions in human and plant kingdom. Some pathogenic fungi such as Malassezia furfur give rise to an unhigenic scaling of the skull. Other systemic infections produce debilitating health conditions such as fever and pain. Some fungi are specifically plant pathogens and stunt the growth of plants either sharing their nutrients or interfering with their metabolic pathways. 1,7-Bis(4-hydroxy-3-methoxyphenyl)-3,5-heptanedione is novel inhibitor of fungi growth. It is an effective inhibitor of both human and plant pathogenic fungi. A remarkable purity dependence of the activity was uncovered in this invention. It was found that 1,7-Bis(4-hydroxy-3-methoxyphenyl)-3,5-heptanedione with >99% purity had manifold activity than when it is >95%. Such a large dependence of activity for a small change in purity is a totally unexpected outcome.

DESCRIPTION OF PRIOR ART

Human mycoses may be broadly classified based on the location of the infection within the body as (i) Superficial, cutaneous and subcutaneous; and (ii) Systemic.

Superficial mycoses include cosmetic fungal infections of the skin or hair shaft with no involvement of living tissues or cellular (immunological or pathological) responses from the host. Cutaneous mycoses are superficial fungal infections of the skin, hair or nails. No living tissue is invaded, however a variety of pathological changes occur in the host because of the presence of the infectious agent and its metabolic products.

An overview of the common pathogens associated with Superficial and cutaneous mycoses is presented herein below as Table A.

| Disease | Causative organisms | Incidence |
| --- | --- | --- |
| I. SUPERFICIAL MYCOSES | | |
| Pityriasis versicolor Seborrhoeic dermatitis including Dandruff and Follicular pityriasis | Malassezia furfur (a lipophilic yeast) | Common |
| Tinea nigra | Exophiala werneckii | Rare |
| White piedra | Trichosporon beigelii | Common |
| Black piedra | Piedraia hortae | Rare |
| II. CUTANEOUS MYCOSES | | |
| Dermatophytosis Ringworm of the scalp, glabrous skin and nails. | Dermatophytes (Microsporum, Trichophyton, Epidermophyton) | Common |
| Candidiasis of skin, mucous membranes and nails. | Candida albicans and related species | Common |
| Dermatomycosis | Non-dermatophyte moulds Hendersonula toruloidea Scytalidium hyalium Scopulariopsis brevicaulis | Rare |

Therapeutic management of superficial and cutaneous fungal diseases has posed a tremendous challenge owing to the fact that fungal cells, like other living organisms, may become resistant to toxic compounds. Antifungal resistance may be defined as a stable, inheritable adjustment by a fungal cell to an antifungal agent, resulting in a less than normal sensitivity to that antifungal. Variable results on the anti-fungal resistance (both clinical and in-vitro resistance patterns) among dermatophytes has been indicated in many prior art references. Some important ones are included herein below.

I. Mycoses. 2007 July; 50(4):286-9

In vitro activities of four antifungal drugs against *Trichophyton rubrum* isolates exhibiting resistance to fluconazole. Santos D A, Hamdan J S. Department of Microbiology, Institute of Biological Sciences, Federal University of Minas Gerais, Belo Horizonte, Minas Gerais, Brazil.

Summary:

Variable MIC ranges for drugs Terbinafine, itakonazole, ketokonazole and griseofulvin against *T. rubrum*, in vitro. Efficacy in the order of Terbinafine>itaconazole>ketoconazole>griseofulvin. Much work is still needed to correlate the MICs of these drugs with clinical outcomes to develop interpretative breakpoints for *T. rubrum* and other dermatophytes.

II. Dermatology. 2003; 207(4):375-80.

Evaluation of in vitro resistance in patients with onychomycosis who fail antifungal therapy.

Gupta A K, Kohli Y. Division of Dermatology, Department of Medicine, Sunnybrook and Women's College Health Science Center, Sunnybrook site and the University of Toronto, Toronto, Ontario, Canada.

Summary:

With the more common use of anti-fungals to treat various fungal infections, development of increased resistance in the causative organisms remains a possibility. However, factors other than fungal resistance may also be implicated in treatment failure.

III. Rev Iberoam Micol. 2007 Dec. 1; 24(4):320-2.

Resistance to azolic compounds in clinical *Trichophyton* spp. Strains. Laboratorio de Investigación Médica en Dermatología y Micología "Dr. Ernesto Macotela", Hospital de Especialidades "Dr. Bernardo Sepúlveda", UMAE Centro Médico Nacional Siglo XXI, IMSS, México D. F., México.

Summary:

Among 36 clinical isolates tested, the resistance to one or more antifungal drugs was demonstrated in seven isolates (19.4%) as follows: three *Trichophyton rubrum*, three *T. mentagrophytes* and one *T. tonsurans*. A *T. rubrum* isolate was resistant to the three azolic drugs; the other six only to fluconazole. It is important to establish the antifungal susceptibility as part of the study procedures in patients with dermatophytosis and a poor antifungal response.

Agricultural mycosis involves the complex relationship between pathogenic fungi and plant hosts in terms of infestation and disease. Agricultural mycosis has also serious implications in terms of the deleterious effects of "mycotoxins" found in agricultural products during the post harvest period. Important mycotoxins include A. Aflatoxins are produced by *Aspergillus* species, and are largely associated with commodities such as groundnuts, other edible nuts, figs, spices and maize. Aflatoxin B1 is a potent carcinogen associated with liver cancer.

B. Ochratoxin A produced by *Penicillium verrucosum* and *Aspergillus ochraceus*, and a contaminant of a wide range of commodities including cereals and their products, fruit and a wide range of beverages and spices.

C. *Fusarium* toxins (fumonisins, trichothecenes and zearalenone) produced by members of the genus *Fusarium* which infect the grain of developing cereals such as wheat and maize.

In an attempt to study significant differences in the biological properties of greater than 99% pure form of 1,7-Bis(4-hydroxy-3-methoxyphenyl)-3,5-heptanedione in comparison with the corresponding 95% pure form, wherein the greater than 99% pure form of 1,7-Bis(4-hydroxy-3-methoxyphenyl)-3,5-heptanedione does not occur along with 5-Hydroxy-1,7-bis(4-hydroxy-3-methoxyphenyl)-3-heptanone and 3,5-Dihydroxy-1,7-bis(4-hydroxy-3-methoxyphenyl)-heptane, the present inventors have surprisingly proved that the anti-fungal properties of the greater than 99% pure form of 1,7-Bis(4-hydroxy-3-methoxyphenyl)-3,5-heptanedione is significantly enhanced in comparison with the corresponding 95% pure form. Hence the present inventors disclose the use of greater than 99% pure form of 1,7-Bis(4-hydroxy-3-methoxyphenyl)-3,5-heptanedione in the manufacture of medicaments for the treatment of superficial and cutaneous mycoses in humans and also treatment methods thereof. Further, the inventors also disclose the use of greater than 99% pure form of 1,7-Bis(4-hydroxy-3-methoxyphenyl)-3,5-heptanedione to control phytopathogenic infestation (bacteria and fungi) in agricultural crops.

Accordingly, it is the principle object of the present invention to disclose the enhanced anti-fungal properties of greater than 99% pure form of 1,7-Bis(4-hydroxy-3-methoxyphenyl)-3,5-heptanedione in comparison to the corresponding 95% pure form, wherein the greater than 99% pure form of 1,7-Bis(4-hydroxy-3-methoxyphenyl)-3,5-heptanedione does not occur along with 5-Hydroxy-1,7-bis(4-hydroxy-3-methoxyphenyl)-3-heptanone and 3,5-Dihydroxy-1,7-bis(4-hydroxy-3-methoxyphenyl)-heptane.

It is another object of the present invention to disclose the use of greater than 99% pure form of 1,7-Bis(4-hydroxy-3-methoxyphenyl)-3,5-heptanedione not occurring along with 5-Hydroxy-1,7-bis(4-hydroxy-3-methoxyphenyl)-3-heptanone and 3,5-Dihydroxy-1,7-bis(4-hydroxy-3-methoxyphenyl)-heptane in the manufacture of medicaments for the treatment of superficial/cutaneous mycoses and treatment methods thereof with no residual toxicity and minimal clinical resistance.

It is yet another object of the present invention to disclose methods of controlling phytopathogenic infestations with no residual toxicity by bringing into contact affected parts of plant with compositions comprising greater than 99% pure form of 1,7-Bis(4-hydroxy-3-methoxyphenyl)-3,5-heptanedione, wherein the greater than 99% pure form of 1,7-Bis(4-hydroxy-3-methoxyphenyl)-3,5-heptanedione does not occur along with 5-Hydroxy-1,7-bis(4-hydroxy-3-methoxyphenyl)-3-heptanone and 3,5-Dihydroxy-1,7-bis(4-hydroxy-3-methoxyphenyl)-heptane The present invention fulfills the aforesaid objectives and provides further related advantages.

SUMMARY OF THE INVENTION

The present invention relates to novel and enhanced anti-fungal properties of greater than 99% pure form of 1,7-Bis(4-hydroxy-3-methoxyphenyl)-3,5-heptanedione in comparison with the corresponding 95% pure form, said greater than 99% pure form of 1,7-Bis(4-hydroxy-3-methoxyphenyl)-3,5-heptanedione being devoid of 5-Hydroxy-1,7-bis(4-hydroxy-3-methoxyphenyl)-3-heptanone and 3,5-Dihydroxy-1,7-bis(4-hydroxy-3-methoxyphenyl)-heptane. The inventors disclose the uses of greater than 99% pure form of 1,7-Bis(4-hydroxy-3-methoxyphenyl)-3,5-heptanedione as anti-fungal agents capable of inhibiting superficial and cutaneous mycoses in humans and treatment methods thereof. Also disclosed is the enhanced potential of greater than 99% pure form of 1,7-Bis(4-hydroxy-3-methoxyphenyl)-3,5-heptanedione as compared to the corresponding 95% pure form against bacterial and fungal phytopathogens and applications thereof in agriculture. Fungal infections are responsible for several disease conditions in human and plant kingdom. Some pathogenic fungi such as Malassezia furfur give rise to an unhigenic scaling of the skull. Other systemic infections produce debilitating health conditions such as fever and pain. Some fungi are specifically plant pathogens and stunt the growth of plants either sharing their nutrients or interfering with their metabolic pathways. 1,7-Bis(4-hydroxy-3-methoxyphenyl)-3,5-heptanedione is novel inhibitor of fungi growth. It is an effective inhibitor of both human and plant pathogenic fungi. A remarkable purity dependence of the activity was uncovered in this invention. It was found that 1,7-Bis(4-hydroxy-3-methoxyphenyl)-3,5-heptanedione with >99% purity had manifold activity than when it is >95%. Such a large dependence of activity for a small change in purity is a totally unexpected outcome.

The present invention provides the following advantages.
1. Disclosure of the enhanced biological (anti-fungal) properties of greater than 99% pure form of 1,7-Bis(4-hydroxy-3-methoxyphenyl)-3,5-heptanedione in comparison to the corresponding 95% pure form.
2. Disclosure of a new therapeutic use for greater than 99% pure form of 1,7-Bis(4-hydroxy-3-methoxyphenyl)-3,5-heptanedione with minimal toxicity in the management of superficial and cutaneous mycoses in the light of increasing anti-fungal resistance to Terbinafine, itakonazole, ketoconazole and griseofulvin and concerns over residual toxicity.
3. Disclosure of novel applications for greater than 99% pure form of 1,7-Bis(4-hydroxy-3-methoxyphenyl)-3, 5-heptanedione with minimal toxicity in controlling phytopathogens (bacteria and fungi).

Other features and advantages of the present invention will become apparent from the following more detailed description, taken in conjunction with the accompanying images, which illustrate, by way of example, the principle of the invention.

DETAILED DESCRIPTION OF THE MOST PREFERRED EMBODIMENT

Figure 1:
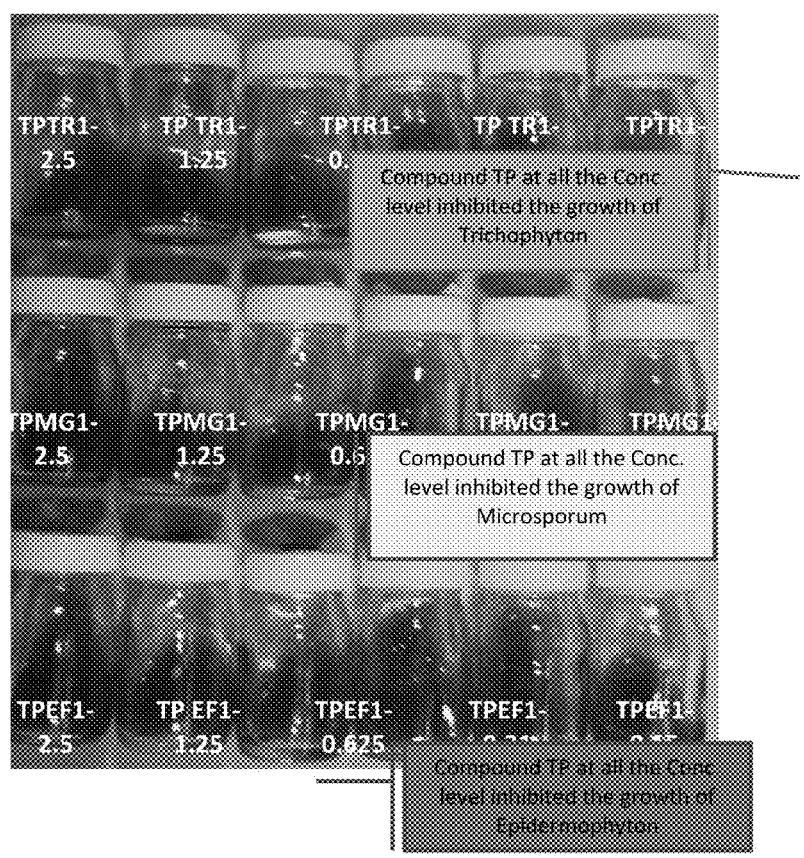
FIG. 1 (Photograph 1) shows the anti-dermatophytic activity of greater than 99% pure form of 1,7-Bis(4-hydroxy-3-methoxyphenyl)-3,5-heptanedione at concentrations of 0.15%, 0.31%, 0.625%, 1.25%, 2.50% and 5.0%, completely inhibiting the growth of *Trichophyton rubrum, Microsporum gypseum* and *Epidermophyton floccosum* both at low and higher concentrations.

In the most preferred embodiment, the present invention relates to the use of greater than 99% pure form of 1,7-Bis(4-hydroxy-3-methoxyphenyl)-3,5-heptanedione represented by STR#1 in the manufacture of a medicament for the treatment of cutaneous mycoses in humans, said greater than 99% pure form of 1,7-Bis(4-hydroxy-3-methoxyphenyl)-3,5-heptanedione showing enhanced anti-fungal activity than the corresponding 95% pure form, on account of being devoid of 5-Hydroxy-1,7-bis(4-hydroxy-3-methoxyphenyl)-3-heptanone represented by STR#II or 3,5-Dihydroxy-1,7-bis(4-hydroxy-3-methoxyphenyl)-heptane represented by STR#III.

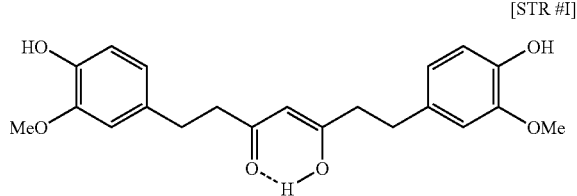

[STR #I]

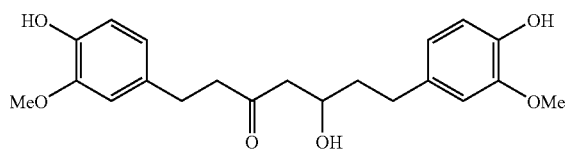

[STR #II]

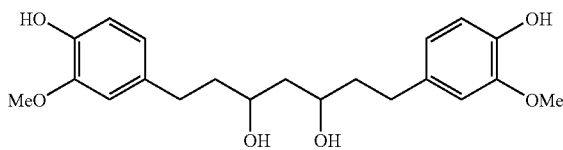

[STR #III]

More specifically, the cutaneous mycoses condition is one selected from the group consisting of Tinea pedis, Tines corporis, Tinea incognito, Tinea unguium (dermatophyte onychomycosis), Tinea capitis, Tinea barbae and candidosis of skin, hair or nails. Further, the cutaneous mycosis condition is dermatophytosis caused by the members of the genus *Trichophyton, Microsporum* and *Epidermophyton*. Still further, the cutaneous mycoses condition is candidosis of hair, skin and nails causes by members of the genus *Candida*. Preferably, said medicament for the treatment of cutaneous mycoses comprises greater than 99% pure form of 1,7-bis(4-hydroxy-3-methoxyphenyl)-3,5-heptanedione at a concentration range of about 0.15% to about 5%. More preferably, the said medicament for the treatment of cutaneous mycoses comprises greater than 99% pure form of 1,7-bis(4-hydroxy-3-methoxyphenyl)-3,5-heptanedione at a concentration of about 0.15%. Further, the said medicament additionally comprises 0.01-0.1% tetrahydropiperine as a bioavailability enhancer.

In another preferred embodiment, the present invention relates to the method of treating cutaneous mycoses in humans, said method involving the step of topically applying to the affected area a formulation comprising 0.1-10% w/w of greater than 99% pure form of 1,7-Bis(4-hydroxy-3-methoxyphenyl)-3,5-heptanedione represented by STR#1, said greater than 99% pure form of 1,7-Bis(4-hydroxy-3-methoxyphenyl)-3,5-heptanedione showing enhanced anti-fungal activity than the corresponding 95% pure form, on account of being devoid of 5-Hydroxy-1,7-bis(4-hydroxy-3-methoxyphenyl)-3-heptanone represented by STR#II and 3,5-Dihydroxy-1,7-bis(4-hydroxy-3-methoxyphenyl)-heptane represented by STR#III. More preferably, the said formulation comprises from about 0.15% to about 5.0% of greater than 99% pure form of 1,7-Bis(4-hydroxy-3-methoxyphenyl)-3,5-heptanedione represented by STR#1. Most preferably, the said formulation comprises 0.15% of greater than 99% pure form of 1,7-Bis (4-hydroxy-3-methoxyphenyl)-3,5-heptanedione represented by STR#1. Further, the said medicament additionally comprises 0.01-0.1% tetrahydropiperine as a bioavailability enhancer.

In yet another preferred embodiment, the present invention relates to the use of greater than 99% pure form of 1,7-Bis(4-hydroxy-3-methoxyphenyl)-3,5-heptanedione represented by STR#1 in the manufacture of a medicament for the treatment of superficial mycoses in humans, said greater than 99% pure form of 1,7-Bis(4-hydroxy-3-methoxyphenyl)-3,5-heptanedione showing enhanced anti-fungal activity than the corresponding 95% pure form, on account of being devoid of 5-Hydroxy-1,7-bis(4-hydroxy-3-methoxyphenyl)-3-heptanone represented by STR#II and 3,5-Dihydroxy-1,7-bis(4-hydroxy-3-methoxyphenyl)-heptane represented by STR#III.

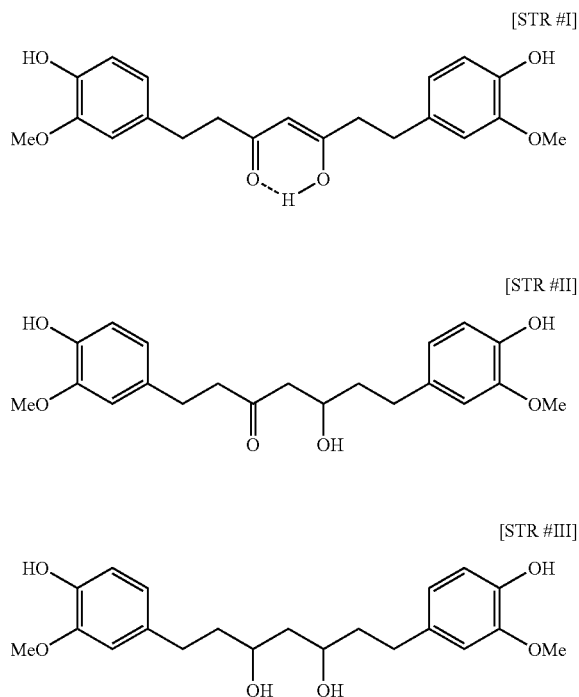

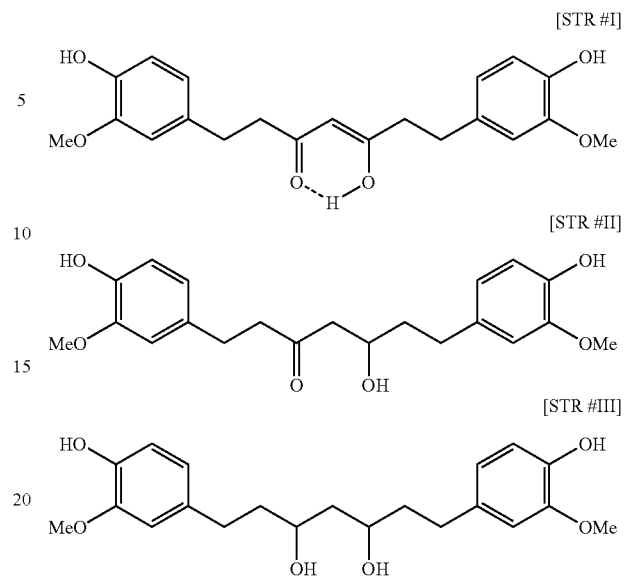

In specific, the superficial mycoses condition is one selected from the group consisting of Pityriasis versicolor, Seborrhoeic dermatitis including Dandruff and Follicular pityriasis, Tinea nigra, White piedra and Black piedra. More specifically, the superficial mycoses condition is caused by Malassezia furfur. Still more specifically, the superficial mycoses condition is caused by Exophiala werneckii. Still more specifically, the superficial mycoses condition is caused by Trichosporon beigelii. Still more specifically, the superficial mycoses condition is caused by Piedraia hortae. Preferably, said medicament for the treatment of superficial mycoses comprises greater than 99% pure form of 1,7-bis(4-hydroxy-3-methoxyphenyl)-3,5-heptanedione at a concentration range of about 0.15% to about 5%. More preferably, the said medicament for the treatment of superficial mycoses comprises greater than 99% pure form of 1,7-bis(4-hydroxy-3-methoxyphenyl)-3,5-heptanedione in a concentration range of about 0.15%. Further, the said medicament additionally comprises 0.01-0.1% tetrahydropiperine.

In another preferred embodiment, the present invention relates to the method of treating superficial mycoses in humans, said method comprising the step of topically applying to the affected area a formulation comprising greater than 99% pure form of 1,7-bis(4-hydroxy-3-methoxyphenyl)-3,5-heptanedione represented by STR#1 in a concentration range of about 0.15% to about 5%, wherein said greater than 99% pure form of 1,7-Bis(4-hydroxy-3-methoxyphenyl)-3,5-heptanedione shows enhanced anti-fungal activity than the corresponding 95% pure form, on account of being devoid of 5-Hydroxy-1,7-bis(4-hydroxy-3-methoxyphenyl)-3-heptanone represented by STR#II and 3,5-Dihydroxy-1,7-bis(4-hydroxy-3-methoxyphenyl)-heptane represented by STR#III.

In an alternate embodiment, the present invention also relates to a method of controlling pathogenic infestation of agricultural crops, said method comprising the step of bringing into contact the infected parts of the plants with 100 ppm (parts per million) to 2000 ppm (parts per million) of a composition comprising greater than 99% pure 1,7-Bis(4-hydroxy-3-methoxyphenyl)-3,5-heptanedione, wherein the said greater than 99% pure form of 1,7-Bis(4-hydroxy-3-methoxyphenyl)-3,5-heptanedione shows enhanced anti-phytopathogenic properties in comparison to the corresponding 95% pure form, on account of being devoid of 5-Hydroxy-1,7-bis(4-hydroxy-3-methoxyphenyl)-3-heptanone and 3,5-Dihydroxy-1,7-bis(4-hydroxy-3-methoxyphenyl)-heptane. Specifically, the phytopathogens are soil borne pathogens or foliar pathogens. More specifically, the phytopathogens are bacteria, fungi and oomycetes. Still more specifically, the phytopathogenic fungi are members of the Phylum Zygomycota, Phylum Ascomycota, Phylum Basidiomycota and Deuteromycetes [Fungi imperfecti]. Further, the phytopathogenic fungi also produce mycotoxins.

The enhanced anti-fungal properties of 0.15% to about 5.0% of 99.5% pure form of 1,7-Bis(4-hydroxy-3-methoxyphenyl)-3,5-heptanedione represented by STR#1 in comparison to the corresponding 95% pure form, on account of being devoid of 5-Hydroxy-1,7-bis(4-hydroxy-3-methoxyphenyl)-3-heptanone represented by STR#II or 3,5-Dihydroxy-1,7-bis(4-hydroxy-3-methoxyphenyl)-heptane represented by STR#III has been highlighted in specific examples included herein below.

Example 1

Anti-Dermatophytic Activity

The anti-dermatophyte efficacy testing for greater than 99% pure form of 1,7-Bis(4-hydroxy-3-methoxyphenyl)-3,5-heptanedione (coded TP) in comparison to the corresponding 95% pure form (coded SW) was done by the agar dilution method. The medium used was Sabouraud's dextrose agar (SDA). Doubling concentration ranges from about 0.15% to about 5% of TP and TW was prepared in 5 ml Dimethylsulfoxide and added to 95 ml of SDA to form a total volume of 100 ml of the medium. The test organisms *Trichophyton rubrum, Microsporum gypseum* and *Epidermophyton floccosum* encoded as TR, MG and EF were inoculated in biosafety level 2 standards into the media comprising test compounds in the specified concentration ranges. Triplicate experiments were set up for each of the three fungi for each concentration of the test compounds to ensure reproducibility of results. DMSO and SDA controls were also included in triplicates for the test.

Figure 2:
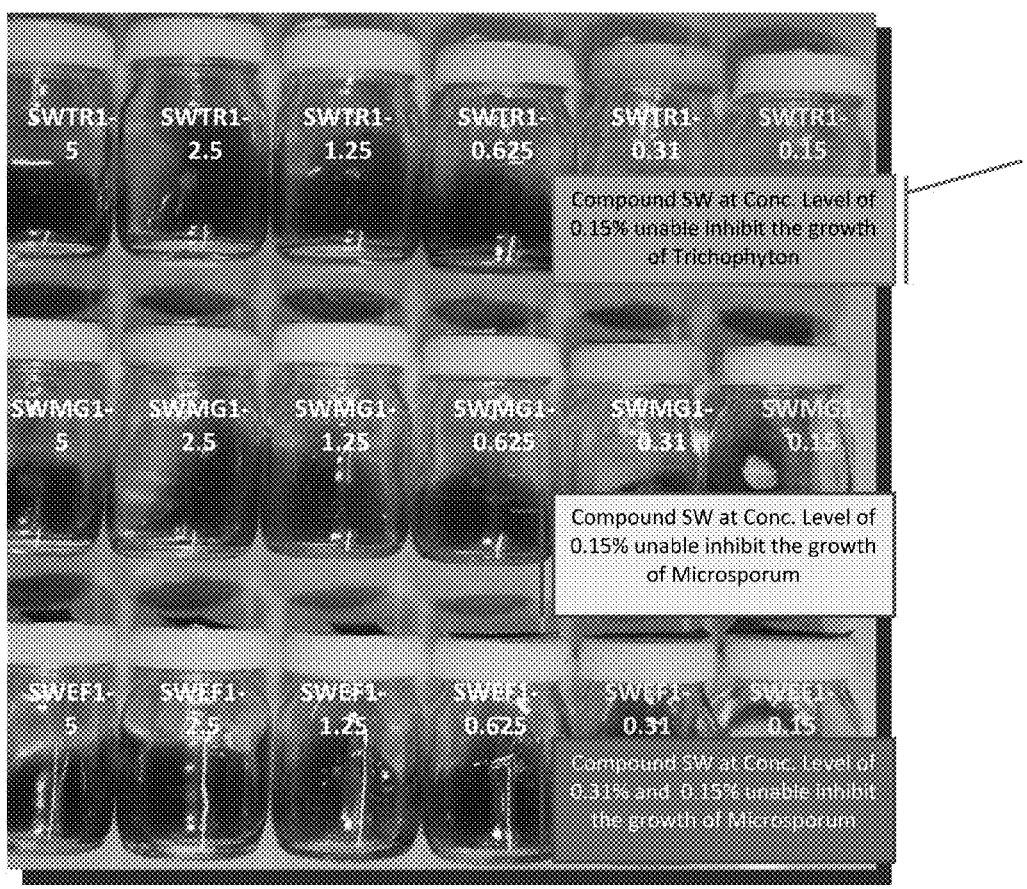
FIG. 2 (Photograph 2) shows the ability of dermatophytes *Trichophyton rubrum, Microsporum gypseum* and *Epidermophyton floccosum* to grow in the presence of lower concentrations (0.15%) of 95% pure form of 1,7-Bis(4-hydroxy-3-methoxyphenyl)-3,5-heptanedione. *Epidermophyton floccosum* is also shown to be tolerant to a slightly higher concentration (0.31%) of 95% pure form of 1,7-Bis(4-hydroxy-3-methoxyphenyl)-3,5-heptanedione.
Figure 3:
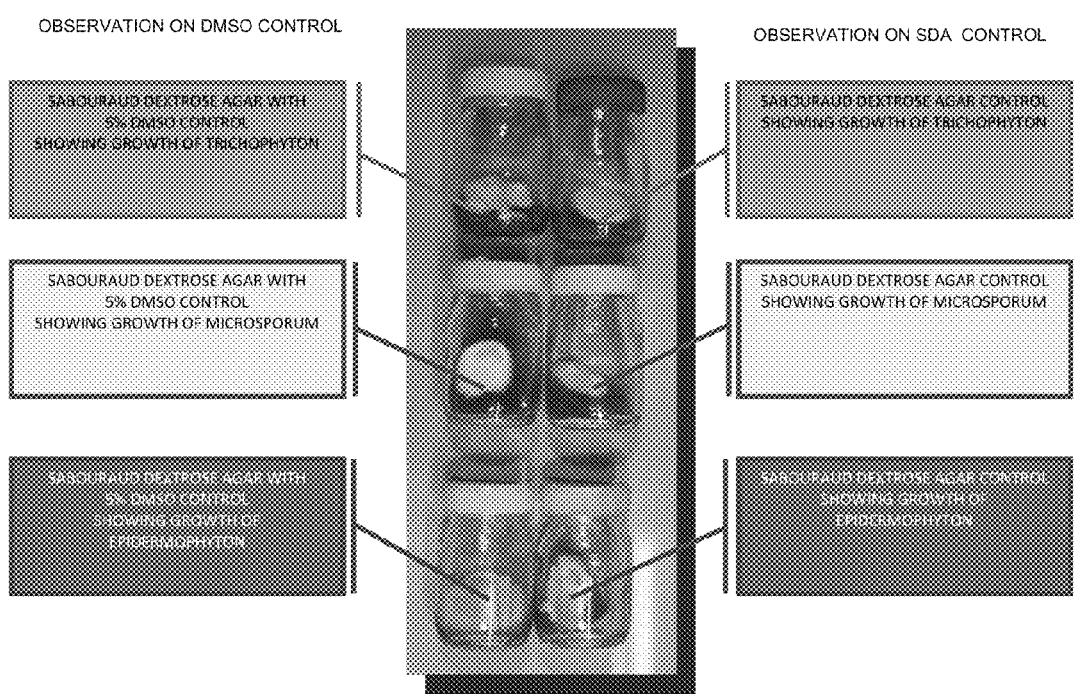
FIG. 3 (Photograph 3) shows no effect of Dimethylsulfoxide (DMSO) used to dissolve the test compounds namely 95% and greater than 99% pure forms of 1,7-Bis(4-hydroxy-3-methoxyphenyl)-3,5-heptanedione on the growth of dermatophytes *Trichophyton rubrum, Microsporum gypseum* and *Epidermophyton floccosum*.

The test results are represented as Table I (FIG. 1, FIG. 2 and FIG. 3). The table may be read as follows. For example, TPTR1 represents growth of *Trichophyton rubrum* in greater than 99% pure form of 1,7-Bis (4-hydroxy-3-methoxyphenyl)-3,5-heptanedione in the first test. Similarly duplicate and triplicate testing are represented as TPTR2 and TPTR3.

TABLE I (FIG. 1, FIG. 2 and FIG. 3)

ANTIFUNGAL EFFICACY - AGAR DILUTION METHOD (Sabourauds Dextrose Agar)

| TEST ORGANISM | TRIAL | COMPOUND TP DMSO SOLVENT WITH FINAL CONCENTRATION | | | | | | COMPOUND SW DMSO SOLVENT WITH FINAL CONCENTRATION |
|---|---|---|---|---|---|---|---|---|
| | | 5% | 2.5% | 1.25% | 0.625% | 0.31% | 0.15% | 5% |
| *Trichophyton rubrum* | TR1 | TPTR1-5 Negative | TPTR1-2.5 Negative | TPTR1-1.25 Negative | TPTR1-0.625 Negative | TPTR1-0.31 Negative | TPTR1-0.15 Negative | SWTR1-5 Negative |
| | TR2 | TPTR2-5 Negative | TPTR2-2.5 Negative | TPTR2-1.25 Negative | TPTR2-0.625 Negative | TPTR2-0.31 Negative | TPTR2-0.15 Negative | SWTR2-5 Negative |
| | TR3 | TPTR3-5 Negative | TPTR3-2.5 Negative | TPTR3-1.25 Negative | TPTR3-0.625 Negative | TPTR3-0.31 Negative | TPTR3-0.15 Negative | SWTR3-5 Negative |
| *Microsporum gypseum* | MG1 | TPMG1-5 Negative | TPMG1-2.5 Negative | TPMG1-1.25 Negative | TPMG1-0.625 Negative | TPMG1-0.31 Negative | TPMG1-0.15 Negative | SWMG1-5 Negative |
| | MG2 | TPMG2-5 Negative | TPMG2-2.5 Negative | TPMG2-1.25 Negative | TPMG2-0.625 Negative | TPMG2-0.31 Negative | TPMG2-0.15 Negative | SWMG2-5 Negative |
| | MG3 | TPMG3-5 Negative | TPMG3-2.5 Negative | TPMG3-1.25 Negative | TPMG3-0.625 Negative | TPMG3-0.31 Negative | TPMG3-0.15 Negative | SWMG3-5 Negative |
| *Epidermophyton flocossun* | EF1 | TPEF1-5 Negative | TPEF1-2.5 Negative | TPEF1-1.25 Negative | TPEF1-0.625 Negative | TPEF1-0.31 Negative | TPEF1-0.15 Negative | SWEF1-5 Negative |
| | EF2 | TPEF2-5 Negative | TPEF2-2.5 Negative | TPEF2-1.25 Negative | TPEF2-0.625 Negative | TPEF2-0.31 Negative | TPEF2-0.15 Negative | SWEF2-5 Negative |
| | EF3 | TPEF3-5 Negative | TPEF3-2.5 Negative | TPEF3-1.25 Negative | TPEF3-0.625 Negative | TPEF3-0.31 Negative | TPEF3-0.15 Negative | SWEF3-5 Negative |

ANTIFUNGAL EFFICACY - AGAR DILUTION METHOD
(Sabourauds Dextrose Agar)

| TEST ORGANISM | TRIAL | COMPOUND SW DMSO SOLVENT WITH FINAL CONCENTRATION | | | | | CONTROL DMSO Control | SDA Control |
|---|---|---|---|---|---|---|---|---|
| | | 2.5% | 1.25% | 0.625% | 0.31% | 0.15% | | |
| *Trichophyton rubrum* | TR1 | SWTR1-2.5 Negative | SWTR1-1.25 Negative | SWTR1-0.625 Negative | SWTR10.31 Negative | SWTR1-0.15 Growth | DMSOTR1 Growth | SDATR1 Growth |
| | TR2 | SWTR2-2.5 Negative | SWTR2-1.25 Negative | SWTR2-0.625 Negative | SWTR2-0.31 Negative | SWTR2-0.15 Growth | DMSOTR2 Growth | SDATR2 Growth |
| | TR3 | SWTR3-2.5 Negative | SWTR3-1.25 Negative | SWTR3-0.625 Negative | SWTR3-0.31 Negative | SWTR3-0.15 Growth | DMSOTR3 Growth | SDATR3 Growth |
| *Microsporum gypseum* | MG1 | SWMG1-2.5 Negative | SWMG1-1.25 Negative | SWMG1-0.625 Negative | SWMG1-0.31 Negative | SWMG1-0.15 Growth | DMSOMG1 Growth | SDAMG1 Growth |
| | MG2 | SWMG2-2.5 Negative | SWMG2-1.25 Negative | SWMG2-0.625 Negative | SWMG2-0.31 Negative | SWMG2-0.15 Growth | DMSOMG2 Growth | SDAMG2 Growth |
| | MG3 | SWMG3-2.5 Negative | SWMG3-1.25 Negative | SWMG3-0.625 Negative | SWMG3-0.31 Growth | SWMG3-0.15 Growth | DMSOMG3 Growth | SDAMG3 Growth |
| *Epidermophyton flocossun* | EF1 | SWEF1-2.5 Negative | SWEF1-1.25 Negative | SWEF1-0.625 Negative | SWEF1-0.31 Growth | SWEF1-0.15 Growth | DMSOEF1 Growth | SDAEF1 Growth |
| | EF2 | SWEF2-2.5 Negative | SWEF2-1.25 Negative | SWEF2-0.625 Negative | SWEF2-0.31 Growth | SWEF2-0.15 Growth | DMSOEF2 Growth | SDAEF2 Growth |
| | EF3 | SWEF3-2.5 Negative | SWEF3-1.25 Negative | SWEF3-0.625 Negative | SWEF3-0.31 Growth | SWEF3-0.15 Growth | DMSOEF3 Growth | SDAEF3 Growth |

It was clearly evident that greater than 99% pure form of 1,7-bis(4-hydroxy-3-methoxyphenyl)-3,5-heptanedione (coded TP) inhibits the growth of dermatophytes *Trichophyton rubrum*, *Microsporum gypseum* and *Epidermophyton flocossum* at all tested concentrations in contrast to 95% pure form of 1,7-bis(4-hydroxy-3-methoxyphenyl)-3,5-heptanedione (coded SW) which was tolerated by the fungi at lower concentrations (0.15%). *Epidermophyton flocossum* was able to grow at both 0.15% and 0.31% of SW.

Example II

Activity Against Malassezia Furfur (Table II)

TABLE II

| ANTIFUNGAL EFFICACY - AGAR DILUTION METHOD (Sabourauds Dextrose Agar with an overlay of coconut oil) COMPOUND TP DMSO SOLVENT WITH FINAL CONCENTRATION | | | | | | | |
|---|---|---|---|---|---|---|---|
| TEST ORGANISM | TRIAL | 5% | 2.5% | 1.25% | 0.625% | 0.31% | 0.15% |
| *Malassezia furfur* (MF) | MF1 | TPMF1 - 5 Negative | TPMF1 - 2.5 Negative | TPMF1 - 1.25 Negative | TPMF1 - 0.625 Negative | TPMF1 - 0.31 Negative | TPMF1 - 0.15 Negative |
| | MF2 | TPMF2 - 5 Negative | TPMF2 - 2.5 Negative | TPMF2 - 1.25 Negative | TPMF2 - 0.625 Negative | TPMF2 - 0.31 Negative | TPMF2 - 0.15 Negative |
| | MF3 | TPMF3 - 5 Negative | TPMF3 - 2.5 Negative | TPMF3 - 1.25 Negative | TPMF3 - 0.625 Negative | TPMF3 - 0.31 Negative | TPMF3 - 0.15 Negative |

| ANTIFUNGAL EFFICACY - AGAR DILUTION METHOD (Sabourauds Dextrose Agar with an overlay of coconut oil) COMPOUND SW DMSO SOLVENT WITH FINAL CONCENTRATION | | | | | | | |
|---|---|---|---|---|---|---|---|
| TEST ORGANISM | TRIAL | 5% | 2.5% | 1.25% | 0.625% | 0.31% | 0.15% |
| *Malassezia furfur* (MF) | MF1 | SWMF1 - 5 Negative | SWMF1 - 2.5 Negative | SWMF1 - 1.25 Negative | SWMF1 - 0.625 Growth | SWMF1 0.31 Growth | SWMF1 0.15 Growth |
| | MF2 | SWMF2 - 5 Negative | SWMF2 - 2.5 Negative | SWMF2 - 1.25 Growth | SWMF2 - 0.625 Growth | SWMF2 - 0.31 Growth | SWMF2 0.15 Growth |
| | MF3 | SWMF3 - 5 Negative | SWMF3 - 2.5 Negative | SWMF3 - 1.25 Negative | SWMF3 - 0.625 Growth | SWMF3 - 0.31 Growth | SWMF3 0.15 Growth |

It was clearly evident that greater than 99% of 1,7-bis(4-hydroxy-3-methoxyphenyl)-3,5-heptanedione in contrast to the corresponding 95% pure form showed enhanced activity against Malassezia furfur at all tested concentration (Table II). It was evident that the 95% pure form could inhibit the growth of the fungus only at higher concentrations (1.25% and above).

Example III

Activity Against *Candida* Species (Table III)

TABLE III

| | Organism: *Candida albicans* NCIM 3471 (yeast) | | | | | |
|---|---|---|---|---|---|---|
| | Concentration of organism (cfu/ml) | | | | Percent Reduction (%) | |
| Test interval (days) | 1,7-bis(4-hydroxy-3-methoxyphenyl)-3,5-heptanedione (>99% purity) | 1,7-bis(4-hydroxy-3-methoxyphenyl)-3,5-heptanedione (about 95% purity) | Nutrient Base | Control | 1,7-bis(4-hydroxy-3-methoxyphenyl)-3,5-heptanedione (>99% purity) | 1,7-bis(4-hydroxy-3-methoxyphenyl)-3,5-heptanedione (about 95% purity) |
| 0 | $14.6 \times 10^5$ | $25 \times 10^5$ | $16.3 \times 10^5$ | $21.7 \times 10^6$ | — | — |
| 7 | $72 \times 10^5$ | $19.7 \times 10^5$ | $83.5 \times 10^5$ | $30.8 \times 10^4$ | 50.6 | 21.2 |
| 14 | $20 \times 10^8$ | $16 \times 10^4$ | $73.5 \times 10^4$ | $12.7 \times 10^4$ | 99.8 | 99.3 |
| 21 | $75 \times 10^2$ | $53 \times 10^5$ | $76.0 \times 10^5$ | $10.5 \times 10^4$ | 99.94 | 78.6 |
| 28 | <130 | $31.5 \times 10^5$ | $82.0 \times 10^6$ | $6.25 \times 10^8$ | 99.99 | 87.4 |

TABLE III-continued

Organism: *Candida albicans* NCIM 3471 (yeast)

| | | | Log Reduction | | | |
|---|---|---|---|---|---|---|
| Test interval (days) | Percent Reduction (%) | | 1,7-bis(4-hydroxy-3-methoxyphenyl)-3,5-heptanedione | 1,7-bis(4-hydroxy-3-methoxyphenyl)-3,5-heptanedione (about | | |
| | Nutrient Base | Control | (>99% purity) | 95% purity) | Nutrient Base | Control |
| 0 | — | — | | | | |
| 7 | 48.7 | 98.5 | 0.5 | 0.2 | 0.5 | 1.8 |
| 14 | 95.4 | 99.4 | 2.8 | 2.3 | 1.5 | 2.4 |
| 21 | 53.3 | 99.5 | 3.4 | 0.7 | 0.53 | 2.5 |
| 28 | 45.6 | 99.9 | 5.3 | 0.8 | 0.5 | 3.7 |

The enhanced efficacy of greater than 99% pure form of 1,7-bis(4-hydroxy-3-methoxyphenyl)-3,5-heptanedione in reducing the colony counts of *Candida albicans* NCIM3471 (Yeast) to less than 100 CFU/ml with an overall percentage reduction of 99.99% over a test interval time of 28 days is indicated in Table III.

Example 4

Activity Against *Fusarium oxysporum* (Table 4)

TABLE 4

1,7-bis(4-hydroxy-3-methoxyphenyl)-3,5-heptanedione (99%) Test Compound

| ORGANISMS | Inoculation Level (CFU/g) | Day 0 count (CFU/g) | Day 7 count (CFU/g) | Day 14 count (CFU/g) | Day 28 Count (CFU/g) |
|---|---|---|---|---|---|
| *Fusarium oxysporum* (mycotoxin producing fungus) | 1 × 10$^7$ | 1 × 10$^7$ | <10 | <10 | <10 |

While the invention has been described with reference to a preferred embodiment, it is to be clearly understood by those skilled in the art that the invention is not limited thereto. Rather, the scope of the invention is to be interpreted only in conjunction with the appended claims.

I claim:

1. A method of treating superficial and cutaneous mycoses in a human, said method comprising topically applying to the affected area of said human a formulation comprising greater than 99% pure form of 1,7-bis(4-hydroxy-3-methoxyphenyl)-3,5-heptanedione.

2. The method according to claim 1, wherein the superficial and cutaneous mycoses condition is selected from a group consisting of Pityriasis versicolor, Seborrhoeic dermatitis, Dandruff, Follicular pityriasis, Tinea nigra, White piedra, Black piedra and onychomycosis.

3. The method according to claim 1, wherein the superficial and cutaneous mycoses are caused by Malassezia furfur, *Trichophyton* species, *Epidermophyton* species, *Microsporum* species, *Candida* or *Aspergillus*.

4. The method according to claim 1, wherein the formulation topically applied additionally contains 0.01-0.1% w/w of tetrahydropiperine.

* * * * *